United States Patent [19]

Blue et al.

[11] Patent Number: 5,310,261
[45] Date of Patent: May 10, 1994

[54] FLUID SPECIMEN CONTAINER

[75] Inventors: Sharon L. Blue, San Clemente, Calif.; Jacob W. Walker, Durham, N.C.

[73] Assignee: Southern California Edison Company, Rosemead, Calif.

[21] Appl. No.: 968,385

[22] Filed: Oct. 29, 1992

[51] Int. Cl.⁵ .............................. A61J 9/02; G01K 1/14
[52] U.S. Cl. ..................................... 374/150; 206/807
[58] Field of Search ......................... 374/150; 128/771; 206/807; 215/366; 283/105

[56] References Cited

U.S. PATENT DOCUMENTS

| | | |
|---|---|---|
| 577,804 | 2/1897 | Witteman . |
| 581,494 | 4/1897 | Schwab . |
| 648,063 | 4/1900 | Bauman ............................. 116/308 |
| 728,735 | 5/1903 | Lowenstein . |
| 1,949,903 | 3/1934 | Fales . |
| 2,422,314 | 6/1947 | Rheinstrom . |
| 2,825,159 | 3/1958 | Schor . |
| 3,623,369 | 11/1971 | Kjellberg ............................ 374/157 |
| 3,750,317 | 8/1973 | Morgan . |
| 4,095,589 | 6/1978 | Manschot et al. ............... 128/771 X |
| 4,306,367 | 12/1981 | Otto .................................... 283/105 X |
| 4,408,905 | 10/1983 | Ehrenkranz . |
| 4,473,530 | 9/1984 | Villa-Real ......................... 128/771 X |
| 4,564,299 | 1/1986 | Ehrenkranz II ................. 128/771 X |
| 4,718,553 | 1/1988 | Adamoli et al. ................. 215/365 X |
| 4,832,046 | 5/1989 | Parrish ................................. 128/771 |
| 4,871,077 | 10/1989 | Ogden et al. ......................... 215/365 |
| 4,878,588 | 11/1989 | Ephraim ........................... 215/365 X |
| 5,064,664 | 11/1991 | Hustad et al. ................... 206/807 X |

Primary Examiner—Daniel M. Yasich
Attorney, Agent, or Firm—Jeffrey G. Sheldon; Denton L. Anderson

[57] ABSTRACT

A container for body fluid specimens includes temperature sensing means and means to read the temperature of a fluid specimen in the container. On the outside face of the container there is a first strip to cover the temperature reading means and over the strip is a label. Removal of the strip defaces or at least partly destroys the label which can indicate tampering with the container.

27 Claims, 1 Drawing Sheet

FLUID SPECIMEN CONTAINER

BACKGROUND

Personnel working in safety sensitive and sporting environments are often subjected to random drug testing, and it is necessary to avoid tampering with specimens.

This invention relates to a tamper-proof container for body fluid specimens such as urine. Different forms of containers have been devised to minimize the possibility of tampering of containers. After rendering the specimen, it is necessary to insure that the particular specimen of the subject is retained in the bottle unadulterated and free of tampering. It is also necessary to insure that there is no substitution of a bottle containing a specimen for a different subject's specimen.

One manner of minimizing sample tampering is to insure that the temperature of the specimen is within a prescribed range within a prescribed period of time after the specimen is rendered. Any major variation in that temperature can indicate that a subject has substituted a rendered specimen with a specimen not immediately rendered.

It is desirable to have a simple system for detecting tampering and thus minimizing the risk of tampering.

Prior art systems use relatively complicated containers with relatively complex closure means operative with a container.

There is a need to provide a simple and effective tamper detection container for fluid body specimens which minimizes the disadvantages of prior art systems.

SUMMARY

By this invention there is provided a container which seeks to provide an effective tamper proof container for body fluid specimens with significant advantages over prior art systems.

According to the invention, a security container for body fluid specimens comprises a base, a container wall and a neck for the container. There is a closure cap for opening and closing the container. A temperature sensing strip is located on the inside of the container. The temperature reading means associated with the strip permits for the temperature of a specimen in the container to be read through the container wall.

First and second removable means covers the temperature reading means. Removal of the first means which is a strip means affects destruction of the second means which is a label. The temperature is readable by removal by both the first and the second means. Thus, unauthorized removal of the first strip means effects defacing of the second means. Specimen collection personnel can thereby assess that the container has been the subject of tampering.

In a preferred form of the invention the container is constituted by an opaque thermoplastic material. The temperature sensing strip is affixed or adhered to the inside of the container. The outer strip selectively adheres to the outside of the container directly over the temperature sensing strip. The label adheres to the container wall and also adheres to the top face of the strip. The outer strip has a portion above the label which facilitates manipulation and its removal from the container wall when desired.

The invention is further described with reference to the accompanying drawings.

DRAWINGS

DESCRIPTION

Figure 1:
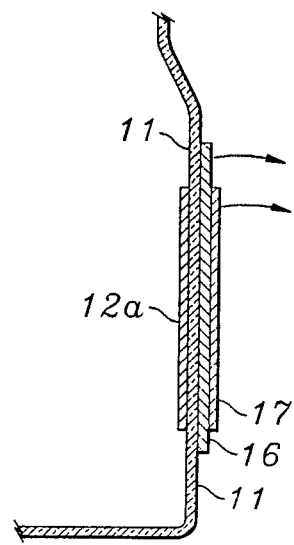
FIG. 1 is a partial sectional side view along line 1—1 of FIG. 2. There is shown the side wall of the container, the base and neck, the temperature strip on the inside wall, the strip on the outside wall and the second label means.
Figure 2:
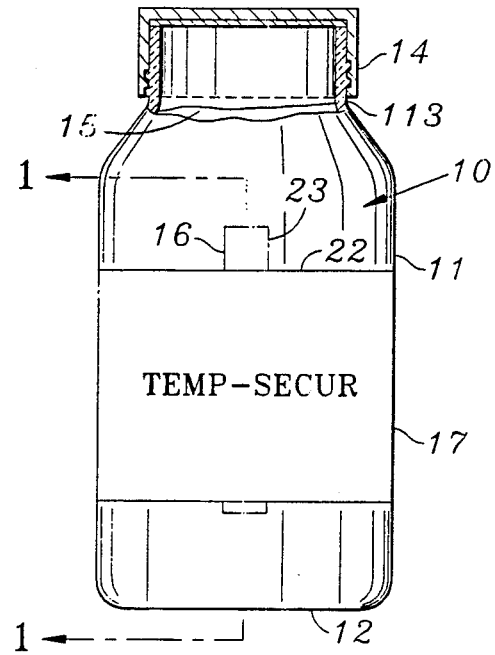
FIG. 2 is a front view, partly in section, of the container showing the strip covered by the label, and the cap for the container.
Figure 3:
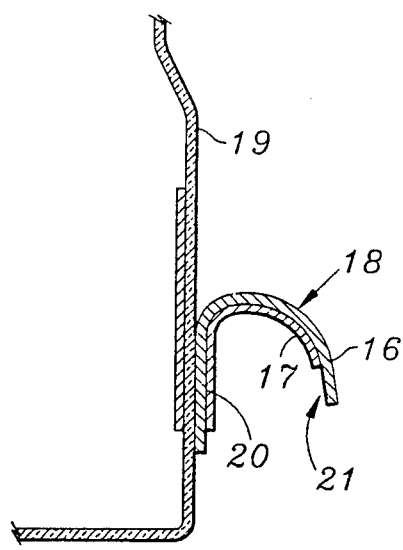
FIG. 3 is a partial sectional side view, similar to FIG. 1, and showing the removal of the outside strip and the label.
Figure 4:
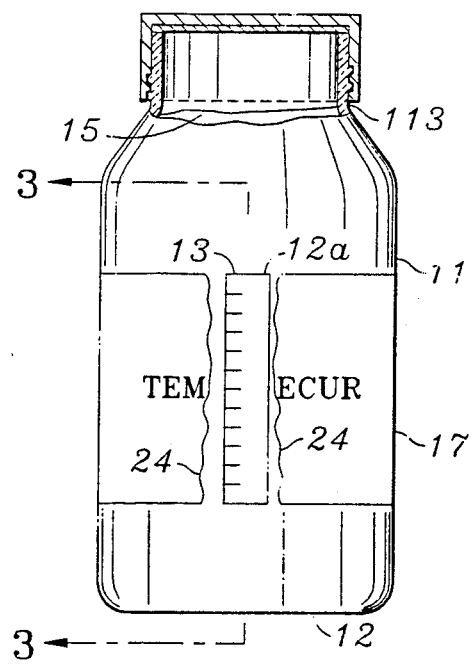
FIG. 4 is a front view of the container similar to FIG. 2 and showing, after removal of the strip, the defaced label and the temperature strip through the wall of the container.

A container bottle 10 for body fluid specimens includes a wall 11, a base 12, and a neck portion 113. On top of the neck there can be located a removable cap 14 for effecting opening and closing of the container 10. The container 10 is formed of a thermoplastic material and is opaque colored so that details of the contents of the container cannot be clearly determined from the outside of the container.

On the inside surface of wall 11 there is adhered a temperature sensing strip 12a with temperature reading means 13. The reading means 13 is a scale extending along the vertically located strip 12a between the base 12 and the neck 13 which will give an indication of the temperature of a specimen 15 contained in the container. The temperature reading means may have values or colors to indicate the temperature. Typically, the container would be thin walled and would hold up to or about 120 milliliters of liquid. The opaque material permits the temperature reading means 13 to be read through the material of the wall 11.

On the outside surface 19 of wall 11 there is a first means constituted by a first means, such as a paper strip 16 which is located substantially parallel with the strip 12a. As such strip 16 covers the temperature sensing strip 12a so that with the strip 16 in place it is not possible to read the temperature scale 13 of strip 12a. Over the strip 16 there is located a second means, such as a paper label 17 which extends at least partly about the circumference of the wall 11 of the bottle 10. The inside face 18 of the strip 16 can have an adhesive material so that it is placed on the outside surface 19 of the wall 11 it adheres in place on the wall. The inner surface 20 of the label 17 also has an adhesive material so that it adheres to the outside face 21 of the strip 16 when it is located over the strip 16.

The label 17 is secured about the mid area of the wall 11 of bottle 10. The strip 16 also extends freely above the top 22 of the removable label 17 to facilitate manipulation thereof. The strip 16 extension selectively does not adhere to the surface 19 of the bottle.

In some alternative embodiments, the strip 16 is affixed to the inside surface 20 of the label 17 and does not adhere to the bottle surface 19. In this manner, when the label 17 is applied to the outer surface 19 of the wall 11 the strip 16 is simultaneously located on the surface 19 of the wall 11.

Effective sensing of the temperature of the specimen 15 can be made by the temperature strip 12a by either filling with specimen 15 to the top 22 of the label or by tilting the bottle enabling specimen 15 to cover label 15.

Following rendering of a specimen 15, namely filling the bottle container 10 with urine, a specimen is presented to an official involved in the collection process. The temperature of the specimen 15 is read by the official and is recorded on a chain-of-custody collection form. In this manner, there has been minimum opportunity for tampering a specimen.

The label 17 extends to about 1 inch circumferentially about, namely to either side of, the temperature strip 12a. In order to reveal the temperature strip 12a, the collection official tears off the strip 16 by holding, with his/her fingers, the tab 23 which is the topmost portion of the strip 16. The strip 16 is pulled downwardly and this tears the label 17 along lines 24 thereby revealing the temperature reading scale 13 of the strip 12a.

The strip 16 can be formed on an opaque or colored material to prevent any possible reading of the temperature through the label 17 and also to clearly be visible to the official. The contrast in colors enhances the ability to detect tampering. Should a person who has rendered a sample wish to find out the temperature of the sample specimen 15 prior to presenting the container 10 to the official, this will be evident since the label 17 will be defaced or torn as indicated by lines 24.

Many other forms of the invention exist, only differing from the others in matters of detail only. For instance, instead of a paper strip 16, the strip may be formed of a different material. Also, instead of a strip, a different shape, element 16 can be used so long as it covers the temperature reading means. Essentially, there are two layers over the temperature reading means.

The invention is defined solely by the following claims.

We claim:

1. A container for a body fluid specimen comprising a base, a wall, and a neck, removable closure means for permitting opening and closing the container, temperature sensing means for sensing the temperature of fluid in the container and a temperature reading means for permitting determination of the temperature of fluid, and first and second removable means covering the temperature reading means whereby removal of the first means effects at least partial removal or destruction of the second means and wherein the temperature is readable by removal of at least part of the first means and at least part of the second means.

2. A container as claimed in claim 1 wherein the container is formed by a thermoplastic material at least partly opaque.

3. A container as claimed in claim 1 wherein the second means is a label secured at least partly about the wall.

4. A container as claimed in claim 3 wherein a temperature reading strip extends for at least part of the length of the first strip.

5. A container as claimed in claim 4 wherein the container is formed by a thermoplastic material at least partly opaque.

6. A container as claimed in claim 5 wherein the temperature reading strip is affixed to an inside wall and the first means is a strip affixed to the outside wall along at least part of the length of the temperature strip, and wherein the top of the first strip is free to facilitate manipulation.

7. A container as claimed in claim 3 wherein the container is formed by a thermoplastic material at least partly opaque.

8. A container as claimed in claim 3 wherein the temperature reading strip is affixed to an inside wall and the first means is a strip affixed to the outside wall long at least part of the length of the temperature strip, and wherein the top of the first strip is free to facilitate manipulation.

9. A container as claimed in claim 3 wherein the second means is a label, the label adhering at least partly on the outside adjacent surface of the wall of the container and at least partly to the outer face of the first means strip.

10. A container for a body fluid specimen comprising a base, a wall, and a neck, removable closure means for permitting opening and closing the container, temperature sensing means for sensing the temperature of fluid in the container and a temperature reading means for permitting determination of the temperature of fluid, and first and second removable means covering the temperature reading means whereby removal of the first means effects at least partial removal or destruction of the second means and wherein the temperature is readable by removal of at least part of the first means and at least part of the second means, wherein the first means is a strip located substantially over the temperature reading means, the temperature reading means being formed on a temperature sensitive strip, the strips being substantially vertically directed between the base and the neck.

11. A container as claimed in claim 10 wherein the second means is a label secured at least partly about the wall.

12. A container as claimed in claim 10 wherein a temperature reading strip extends for at least part of the length of the first strip.

13. A container as claimed in claim 10 wherein the temperature reading strip is affixed to an inside wall and the first means is a strip affixed to the outside wall long at least part of the length of the temperature strip, and wherein the top of the first strip is free to facilitate manipulation.

14. A container as claimed in claim 13 wherein the second means is a label, the label adhering at least partly on the outside adjacent surface of the wall of the container and at least partly to the outer face of the first means strip.

15. A container as claimed in claim 10 wherein the second means is a label, the label adhering at least partly on the outside adjacent surface of the wall of the container and at least partly to the outer face of the first means strip.

16. A container as claimed in claim 10 wherein the container is formed by a thermoplastic material at least partly opaque.

17. A container as claimed in claim 10 wherein the temperature reading strip is affixed to an inside wall and the first means is a strip affixed to the outside wall along at least part of the length of the temperature strip, and wherein the top of the first strip is free to facilitate manipulation.

18. A container for a medical fluid specimen comprising a base, a wall, and a neck, removable closure means for engaging the neck for permitting opening and closing the container, temperature sensing means affixed in the container for sensing the temperature of fluid in the container and temperature reading means for permitting determination of the temperature of fluid through the wall of the container, a removable strip and a label covering the temperature reading means whereby removal of the strip effects at least partial removal or destruction of the label and wherein the temperature is readable by removal of at least part of the strip and at least part of the label.

19. A container as claimed in claim 18 wherein the strip is affixed to the label, and wherein a portion of the strip extends beyond the label, the extended portion not being affixed to the label and being selectively affixed to the container wall.

20. A container as claimed in claim 18 wherein a temperature reading strip extends for at least part of the length of the first strip.

21. A container as claimed in claim 18 wherein the container is formed by a thermoplastic material at least partly opaque.

22. A container as claimed in claim 18 wherein the temperature reading strip is affixed to an inside wall and the first means is a strip affixed to the outside wall long at least part of the length of the temperature strip, and wherein the top of the first strip is free to facilitate manipulation.

23. A container as claimed in claim 18 wherein the second means is a label, the label adhering at least partly on the outside adjacent surface of the wall of the container and at least partly to the outer face of the first means strip.

24. A bottle for a body fluid specimen comprising a container, removable closure means for permitting opening and closing the container, temperature sensing strip affixed to the inside of the container for sensing the temperature of fluid in the container and for permitting indication of the temperature of fluid through the wall of the container, a removable strip and a label covering the temperature indication whereby at least partial removal of the strip effects removal of the label and wherein the temperature is indicated by removal of at least part of the strip and at least part of the label.

25. A container for a body fluid specimen comprising a base, a wall, and a neck, removable closure means for permitting opening and closing the container, temperature sensing means for sensing the temperature of fluid in the container and a temperature reading means for permitting determination of the temperature of fluid, and first and second removable means covering the temperature reading means whereby removal of the first means effects at least partial removal or destruction of the second means, and wherein the temperature is readable by removal of at least part of the first means and at least part of the second means, and wherein the first means is located substantially over the temperature reading means, the temperature reading means being formed on a temperature sensitive means.

26. A container for a medical fluid specimen comprising a base, a wall, and a neck, removable closure means for engaging the neck for permitting opening and closing the container, temperature sensing means affixed in the container for sensing the temperature of fluid in the container and temperature reading means for permitting determination of the temperature of fluid through the wall of the container, and a removable means on the wall and substantially covering the temperature reading means, wherein the temperature is readable by at leas partial removal of the removable means.

27. A container for a medical fluid specimen comprising a base, a wall, and a neck, removable closure means for engaging the neck for permitting opening and closing the container, temperature sensing strip means affixed in the container for sensing the temperature of fluid in the container and temperature reading means for permitting determination of the temperature of fluid through the wall of the container, a removable means covering the temperature reading means wherein the temperature is readable by at least partial removal of removable means, and the temperature reading means being substantially vertically directed in part between the base and the neck.

* * * * *